Figure 2A:
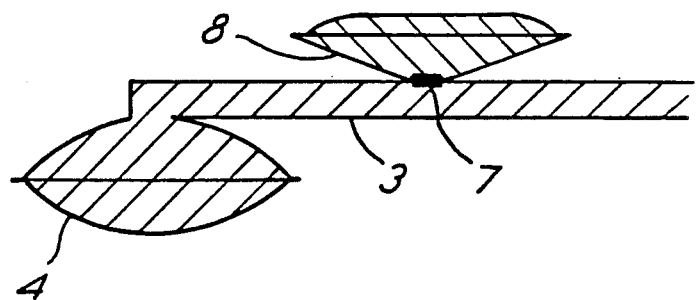

United States Patent [19]

Baker et al.

[11] Patent Number: 5,064,618

[45] Date of Patent: Nov. 12, 1991

[54] SENSOR ARRANGEMENTS

[75] Inventors: Christopher J. S. Baker, Richmond; Peter D. Whalley, Slough, both of England

[73] Assignee: Thorn EMI plc, London, England

[21] Appl. No.: 236,911

[22] Filed: Aug. 26, 1988

[30] Foreign Application Priority Data

Aug. 29, 1987 [GB] United Kingdom ............... 8720470

[51] Int. Cl.$^5$ ............................................. G01N 27/00
[52] U.S. Cl. ................... 422/82.01; 204/400; 204/406; 204/407; 204/409; 204/410; 204/411; 204/412; 204/416; 204/422; 422/68.1; 422/82.03
[58] Field of Search ............... 422/68.1, 82.01, 82.03; 204/400, 406, 407, 416, 409-412, 422

[56] References Cited

U.S. PATENT DOCUMENTS 4,336,121 6/1982 Enzer et al. ..................... 422/82.01
4,342,964 8/1982 Diamond et al. .
4,397,725 8/1983 Enzer .
4,654,127 3/1987 Baker et al. ..................... 422/82.01

FOREIGN PATENT DOCUMENTS 0122420 10/1984 European Pat. Off. .
WO85/02257 5/1985 PCT Int'l Appl. .

Primary Examiner—Robert J. Warden
Assistant Examiner—Timothy M. McMahon
Attorney, Agent, or Firm—Fleit, Jacobson, Cohn, Price, Holman & Stern

[57] ABSTRACT

A disposable cartridge for use in a clinical sensing arrangement interfaces electrically with a host instrument capable of responding to electrical signals generated by detector devices incorporated in the cartridge upon exposure to calibrant fluids and/or clinical fluids under examination. The cartridge includes a passage linking a reservoir of calibrant fluid to the detector devices and further linking the device to a closed container for fluid which has been conveyed past the devices. A fluid under test can be introduced into the cartridge through the passage wall at a location disposed between the reservoir and the detector devices.

7 Claims, 2 Drawing Sheets

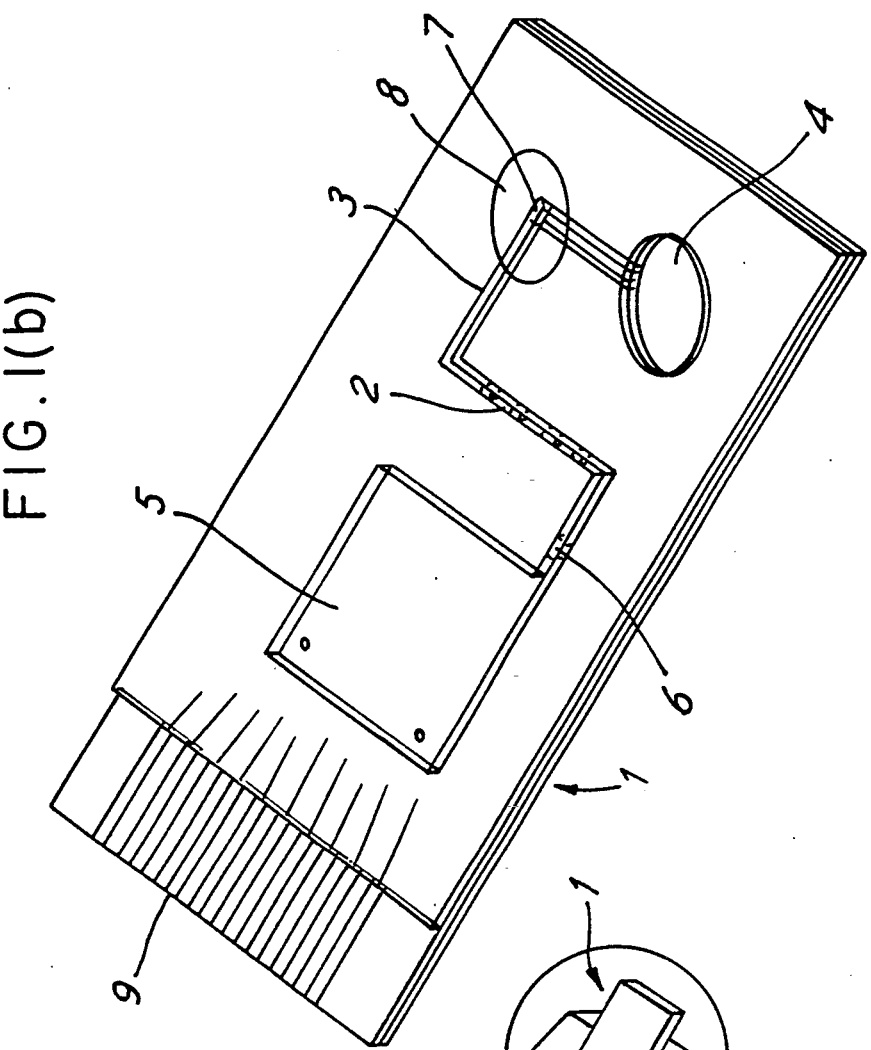
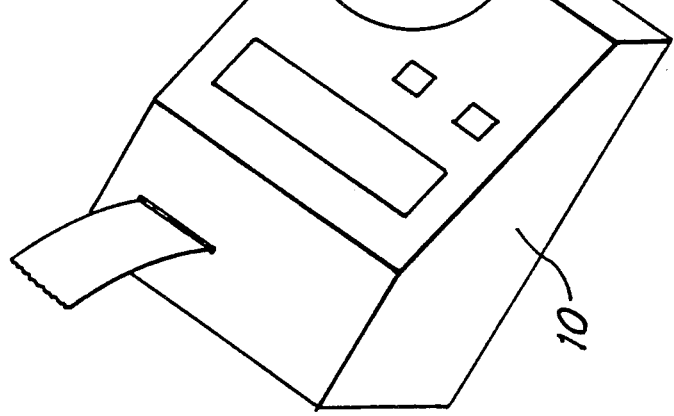
FIG. 1(a)
FIG. 1(b)

SENSOR ARRANGEMENTS

This invention relates to sensor arrangements, and it relates especially, though not exclusively, to such arrangements as may be used for the clinical testing of sample body fluids.

Miniature sensors, such as those incorporating ion selective field-effect transistor (ISFET) technology are showing promise in the field of clinical analysis, the major difficulties associated with the use of miniature sensors for these purposes being associated with the presentation to the sensing devices of calibrant and body fluids. This invention aims to reduce such difficulties and, at the same time, to deal with the problems of hygenic handling and convenient and secure disposal of the body fluids in question.

The invention is concerned in principle with an arrangement whereby certain components of a sensor arrangement that can be re-used time after time are incorporated into a host instrument, and a disposable unit, conveniently referred to as a "cartridge" and which contains one or more sensing devices, means for presenting calibrant and body fluids to the device or devices and a waste receptacle, is designed to interface with the host instrument. The disposable cartridge is intended for once only usage.

In particular, the invention provides a disposable cartridge for use in an arrangement of the kind just described, the cartridge comprising a reservoir of calibrant fluid, a sensor device, a passage linking said reservoir to said device, means for introducing a fluid for analysis into said passage, means for causing said fluid to flow sequentially (in either order) past said device and a closed container, linked to said passage, to collect said fluids after they have passed said device.

Figure 2B:
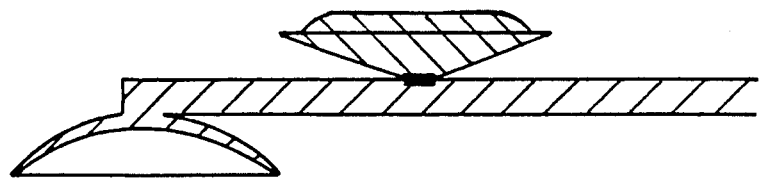
Figure 2C:
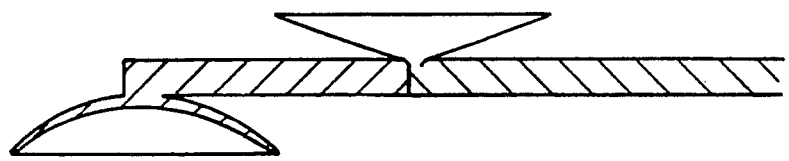

In order that the invention may be clearly understood and readily carried into effect, one embodiment thereof will now be described, by way of example only, with reference to the accompanying drawings of which:

FIG. 1 shows a disposable cartridge in accordance with one example of the invention, together with a host instrument, and FIG. 2 shows, in schematic form, part of the disposable cartridge of FIG. 1.

Referring now to the drawings, in both of which common features are identified by common reference numbers, a disposable cartridge in accordance with one example of the invention is shown at 1 and is made of a "sandwiched" construction of plastics materials.

An array of ISFET sensors is shown at 2, these sensors being disposed in, or at least having their sensitive areas communicating with, a passage 3, in this case a capillary duct. The passage 3 is connected at one of its ends to a reservoir 4 of a calibrant fluid and at its other end to a waste cavity 5. For storage purposes, a plug 6 is disposed within the passage 3 adjacent its connection to the waste cavity 5. This enables the array 2 to be exposed to the calibrant fluid during storage if desired whilst preventing the fluid being accidentally pumped out of the reservoir 4 during the shelf life of the cartridge.

When it is desired to cause the calibrant fluid in reservoir 4 to flow past array 2, the reservoir 4 is compressed, either manually or mechanically, to cause plug 6 to either rupture or be physically displaced into the waste cavity 5. The fluid is drawn past the array by a combination of capillary action of passage 3, pressure exerted on the reservoir 4 and suction created by the provision of absorbent material in waste cavity 5. Additional pumping or suction forces can be applied if desired.

Intermediate the reservoir 4 and the array 2 of sensors, there is provided an access point 7 at which body fluid can be introduced to the passage 3. Conveniently, at this access point, there is provided a thinning of the plastics material used on the top cover of the sandwich construction or a foil is bonded over an aperture in that cover. In either event, a small reservoir 8, preferably conical in shape, is provided into which the body fluid in question can be introduced at the appropriate time. Once the body fluid is in place, and the calibrant fluid has flowed past the array 2, the thinned wall of the cover or the foil, immediately therebeneath is caused to rupture, for example by piercing it, so that the body fluid can enter the passage 3 and be drawn past the array 2 and into the waste cavity by the combined action of capillary flow along passage 3 and suction generated by the absorbent material in waste cavity 5.

The array 2 of sensors interconnects electrically with an array 9 of interface tracks which interconnect with a suitable complementary interface port in a host instrument 10 which is shown in outline only since it could, of course, take a variety of forms. Preferably, the instrument 10 incorporates a thermal plate which is adjacent to the cartridge 1 when coupled to the aforementioned port, and which maintains the test sample at a substantially constant temperature. Electrical signals derived from the sensor array 2 via the interface with the array 9 of tracks are processed by a microprocessor in the instrument 10, and the instrument also houses an internal clock, which provides a time base for operation of the arrangement, a back-up battery power source, an operator keyboard, a display and a printer. It can also be convenient for the instrument 10 to incorporate a reader capable of automatically reading and conveying to the microprocessor data recorded, for example as a bar code, on the cartridge. Such data can include cartridge test type, batch numbers and shelf-life expiry date.

Referring now to FIG. 2, the reservoir 4 can conveniently be constructed in the form of a deformable sac constructed from two curved surfaces joined and hermetically sealed along common edges. The outer face of the sac is at atmospheric pressure. Withdrawal of the calibrant fluid from the sac is prevented by plug 6 (FIG. 1).

Release of the calibrant fluid is initiated by finger pressure of an operator or mechanical means on the external face of the sac. The plug 6 is breached or removed due to the increase of pressure differential across it, which may be enhanced by means of a fluid and/or gas pumping system using mechanical means, gravity or capillary effects or other means.

The sac is a bi-stable structure, configured so that its external face collapses to a stable position against the opposite face of the sac as the calibrant fluid vacates the enclosed volume into the duct 3.

Calibrant fluid flows due to the finger pressure on the sac (enhanced by any pre-existing pressure differential across the plug). When the outer face of the sac has fully deformed against the inner face, the enclosed volume approaches zero. Flow of calibrant fluid is arrested as the pressure differential along the ducting is insufficient to cause a partial vacuum within the fluid-filled duct.

Adjacent to the sac is the access point 7 to the duct 3 for an externally presented fluid. This access comprises an aperture to the duct, sealed as described previously, and the seal is, of course, of sufficient strength to remain intact during the procedure for release of calibrant fluid. The aperture is located at the base of an inverted cone-shaped receptacle 8 into which a quantity of the test fluid is placed.

Perforation of the seal, e.g. by a hypodermic syringe needle, opens the duct 3 to atmospheric pressure, which drives the test fluid into the duct, displacing calibrant fluid before it. The pressure differential driving the fluid may be enhanced by the pumping system noted above.

The dimensions of the collapsible sac and of the ducts may be such as to enable known quantities of fluid to be driven through the ducts at predetermined rates of flow (e.g. exploiting the phenomena associated with capillaries).

Valves may be incorporated within the ducts to prevent reverse flow and to permit fluid separation, e.g. to prevent mixing of calibrant and hydration fluids. (Use of a hydration fluid, to maintain the sensors in readiness for a test whilst in storage, may be preferable to reliance on a calibrant fluid which will be used just prior to a test).

We claim:

1. A disposable cartridge arranged to interface with a host instrument for sensing characteristics of fluids; the cartridge comprising a deformable reservoir; breachable plug means disposed within the passage; at least one sensor device disposed within the passage intermediate the reservoir and the breachable plug means; calibrant fluid held within the reservoir and extending along the passage past the at least one sensor to the breachable plug means; a further reservoir connected to the passage for containing fluid for analysis, the further reservoir including rupturable access means for enabling the fluid for analysis to be introduced into the passage; a container linked to the passage remote from the deformable reservoir; absorbent material disposed within the container; the cartridge arranged such that on deformation of the reservoir, calibrant fluid within the passage breaches the breachable plug means and flows into contact with the absorbent material, which material serves to induce capillary action in the passage, such that on rupturing the rupturable access means, fluid for analysis is drawn into the passage and past the at least one sensor for sensing.

2. A cartridge according to claim 1 comprising electrical edge connector means coupled to said at least one device and configured to interface with complementary connector means supported by said host instrument.

3. A cartridge according to claim 1 wherein the passage comprises a capillary duct, the duct linking the container to the at least one sensor device.

4. A cartridge according to claim 1 wherein the reservoir of calibrant fluid comprises a sac having curved surfaces.

5. A cartridge according to claim 1 wherein the means for introducing fluid for analysis includes access means to the passage, the means for introducing fluid including a rupturably sealed aperture.

6. A sensor arrangement comprising a cartridge according to claim 1 in combination with a host instrument, the host instrument incorporating means to utilise electrical signals derived from the at least one sensor device.

7. An arrangement according to claim 6 wherein the host instrument includes control means to control the temperature of the cartridge when the cartridge is placed in interfacing relationship with the host instrument.

* * * * *